United States Patent [19]

Schmidt

[11] Patent Number: 5,932,207
[45] Date of Patent: *Aug. 3, 1999

[54] COMPLEX ACTIVE INGREDIENT FOR THE PRODUCTION OF BIOLOGICAL PARTS, ESPECIALLY ORGANS FOR LIVING ORGANISMS: METHOD FOR THE PRODUCTION OF THE SAME AND ITS USE

[76] Inventor: Karlheinz Schmidt, Aussere Weiler Strasse 12, 7413 Gomaringen, Germany

[ * ] Notice: This patent is subject to a terminal disclaimer.

[21] Appl. No.: 08/350,666

[22] Filed: Dec. 7, 1994

Related U.S. Application Data

[63] Continuation of application No. 07/849,083, filed as application No. PCT/DE90/00782, Oct. 12, 1990, abandoned.

[30] Foreign Application Priority Data

Nov. 3, 1989 [DE] Germany .............................. 39 36 568

[51] Int. Cl.⁶ .................................................. A61K 45/05
[52] U.S. Cl. ............................ 424/85.1; 514/12; 514/21; 514/22
[58] Field of Search ............................. 424/85.1; 514/21, 514/12, 22

[56] References Cited

U.S. PATENT DOCUMENTS

| | | |
|---|---|---|
| 4,294,753 | 10/1981 | Urist . |
| 4,404,134 | 9/1983 | Becker et al. ........................... 530/356 |
| 4,472,840 | 9/1984 | Jeffries . |
| 4,642,120 | 2/1987 | Nevo et al. ............................... 623/11 |
| 4,681,763 | 7/1987 | Nathanson et al. . |
| 4,693,718 | 9/1987 | Urry et al. ................................ 623/11 |
| 4,703,108 | 10/1987 | Silver et al. ............................. 530/356 |
| 4,732,155 | 3/1988 | Zetter et al. ............................. 128/630 |
| 4,832,686 | 5/1989 | Anderson ................................. 424/85.2 |
| 4,863,732 | 9/1989 | Nathan et al. ............................. 424/95 |
| 4,925,924 | 5/1990 | Silver et al. ............................. 530/356 |
| 4,932,973 | 6/1990 | Gendler ..................................... 623/16 |
| 4,950,483 | 8/1990 | Ksander et al. ......................... 424/422 |
| 4,973,466 | 11/1990 | Reich ....................................... 424/426 |
| 5,019,087 | 5/1991 | Nichols ..................................... 623/13 |
| 5,024,841 | 6/1991 | Chu et al. ................................ 424/422 |
| 5,041,138 | 8/1991 | Vacanti et al. ............................ 623/10 |

FOREIGN PATENT DOCUMENTS

| | | |
|---|---|---|
| 0271668 | 6/1988 | European Pat. Off. . |
| 2637502 | 4/1990 | France . |
| 2137209 | 10/1984 | United Kingdom . |
| 2215209 | 9/1989 | United Kingdom . |
| 8400540 | 2/1984 | WIPO . |
| 8807078 | 9/1988 | WIPO . |
| 9000060 | 1/1990 | WIPO . |

OTHER PUBLICATIONS

Furcht et al., Lab. Investigation, vol. 55 (5) pp. 505–509 (1986) "Editorial: Critical Factors Controlling Angiogenesis . . .".

Dijke et al., "Growth Factors for Wound Healing", Biotechnology, vol. 7, pp. 793–798 (1989).

*Primary Examiner*—Cecilia J. Tsang
*Assistant Examiner*—Patrick R. Delaney
*Attorney, Agent, or Firm*—Blank Rome Comisky & McCauley LLP

[57] ABSTRACT

An active ingredient complex to promote the growth of cells, tissue and/or organs is disclosed. The complex comprises the following form ingredients: a structural component, a recruiting component, an adhesion component and an adherence component.

8 Claims, 1 Drawing Sheet

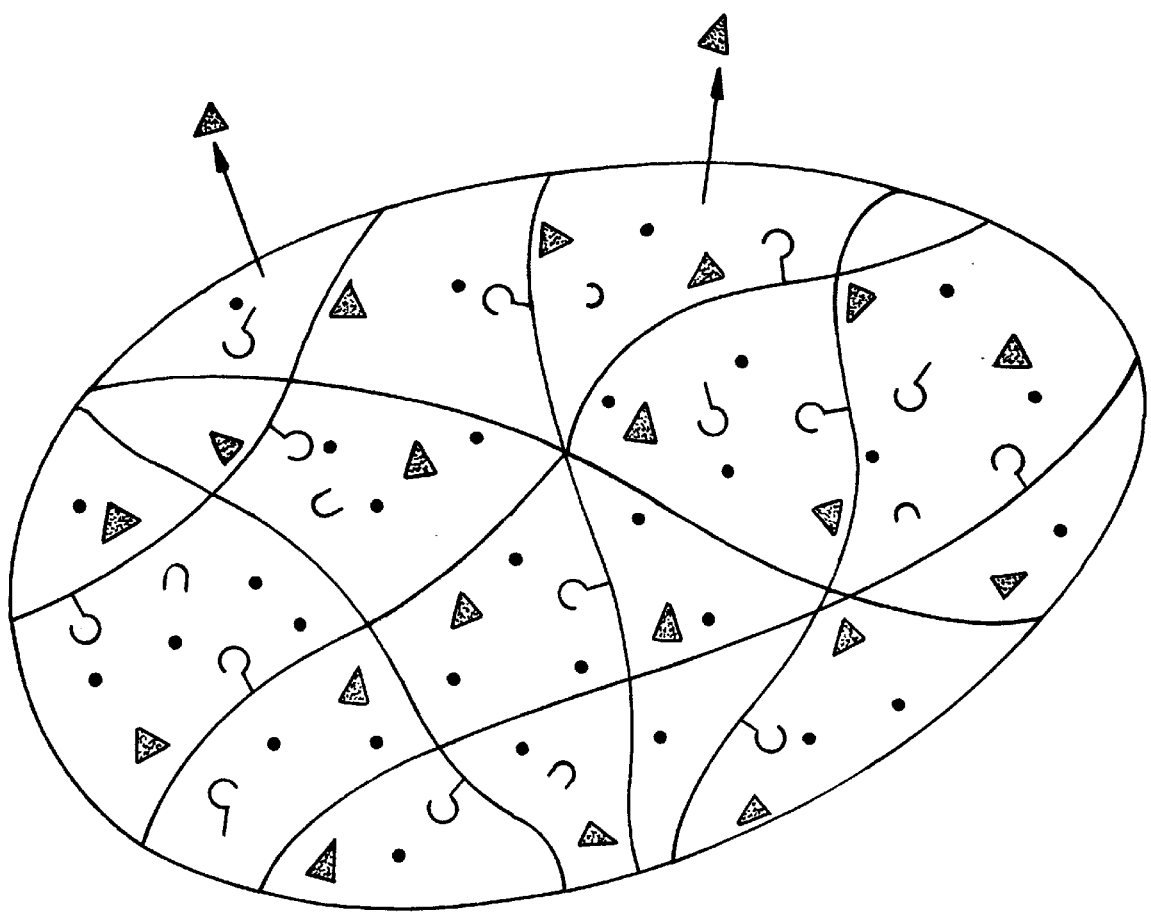

COMPLEX ACTIVE INGREDIENT FOR THE PRODUCTION OF BIOLOGICAL PARTS, ESPECIALLY ORGANS FOR LIVING ORGANISMS: METHOD FOR THE PRODUCTION OF THE SAME AND ITS USE

This is a continuation of application Ser. No. 07/849,083 filed on Sep. 17, 1992 (now abandoned) which is a 371 of PCT/DE90/00782 filed on Oct. 12, 1990.

BACKGROUND OF THE INVENTION

The various functional performances of living organisms (human beings, animals, plants) are usually not diffused over their bodies, but rather are separate and are concentrated according to a characteristic structural and functional plan for each individual type of function taking place in a distinct biological part. These biological parts, the subject of the invention, include organelles, cells, tissue, organs, and parts thereof. Frequently these parts are then combined into complex systems to which the invention likewise makes reference. Examples of such biological parts are muscle tissue, cartilage, bone, liver, spleen, skin, etc. Examples of complex systems are the nervous system, vascular system, skeletal system, hormone system, immune system, etc.

In the course of life and likewise in the formation of the living organism, any living being can be subject to damages of structure and function of individual biological parts up to the point that the part or even the entire system can be completely nonfunctional. This functional failure could among other things be of genetic origin or it could occur because microorganisms such as bacteria, viruses, funguses or parasites have damaged or destroyed the biological parts, because injuries have occurred due to mechanical, chemical, thermal, electric or radiological effects, or because disorders of unknown origin have had an effect on the biological parts in the form of various degenerative processes, cancer or many types of modifications due to age.

The present state of the art is to try to compensate for damages or even for complete loss of function of individual biological parts by application of chemical compounds. In doing so, a deficiency of function or the complete lack of function or functional effectiveness of individual metabolic products which are produced by the relevant biological part is to be compensated. One example of this is the loss of the function or some part of the function of the pancreas, which leads to an insulin deficiency or to a complete failure of the product synthesis of the pancreas. Insulin obtained from animals or produced chemically or biotechnically is used to compensate for the deficiency. This manner of use of chemical compounds or biological synthesis products can only partially compensate for the insufficient performance of functions of biological parts, because only short-term effective deposits of the compound can be placed in the body and there is no regulated release of the materials or synthetic materials into the body to fulfill the instant requirement of the body.

Because of these problems, and especially in the case of the occurrence of damages to a plurality of functional parts or in the case of destruction of an entire biological part, the state of the art also includes the integration of the often life-vital defective or lost functional parts into a technical apparatus and to attach the apparatus to the body or to build it into the body as a prosthesis. Some examples of such auxiliary means in extracorporal use are spectacles, hearing aids, arm or leg prostheses, synthetic kidneys, etc. For intracorporal use, heart pacemakers, blood vessel prostheses, synthetic joints, etc., are known. There are also mixed extra/intracorporal auxiliary parts, such as tooth implants, but ready-to-use prostheses for intracorporal replacement of inner organs such as the artificial heart, artificial pancreas, artificial liver or kidneys, do not yet belong to the state of the art. Basically, a technical replacement for biological parts still remains to be secured, while only partial functions can be replaced and the entire functional performance of such replaced biological parts can never be secured. In addition, the functional capacity of the technical system, in other words, of the prostheses or the artificial organ, cannot be guaranteed over a long period, and its adaptation to changing conditions is not possible as it is with a true biological part. In addition, there are significant acceptance problems, in terms of the tolerance of a foreign body in the organism and also the feeling of dependence on the function of a technical apparatus.

Furthermore, the transplantation of biological parts belongs to the state of the art. In transplantation, a transfer of biological parts within the same organism (autogenic transplantation), a transfer from a donor of the same type as the receiver to said receiver (allogenic transplantation) or a transfer from a donor of a different species from the receiver to said receiver (xenogeneic transplantation) are known.

The possibilities revealed by autogenic transplantation are for the most part limited by the availability of biological parts for a transfer. However, as far as is possible, it is the preferred usage, since it causes no immunological problems. Examples of this transplantation include skin transplants, the autotransfusion of blood, transplantation of muscles, fat tissue, bone, cartilage, blood vessels, etc.

Because of availability, the preferred transplantation is allogenic transplantation. In this field, despite many problems involved with them, blood transfusions have succeeded in a wide range of uses, and in addition to blood banks which have been established for this purpose, now there are also skin and bone banks. Numerous other organs are likewise transplanted allogenically, such as, for instance, kidneys, hearts, livers, pancreases, bone marrow, corneas, etc.

In the case of allogenic and xenogenic transplantation of biological parts however, the problem arises of immunological incompatibility, which leads to rejection by the living organism with respect to the transplant and for the most part constrains the receiver to lifelong intake of immunosuppressive substances with concurrent damaging side effects. Also, there is the continuing danger of transmission of illnesses, since the "living" biological parts cannot be sterilized. With allogenic transplantation therefore the genetic uniformity of the receiver is lost, and the transplantation itself actually becomes chimeric.

SUMMARY OF THE INVENTION

In short, this object is attained by an active ingredient complex comprising a structural component, at least one recruiting component, at least one adhesion component and at least one growth and/or maturation component.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF A PREFERRED EMBODIMENT

The active ingredient complex according to the present invention has the quality of passing over to cells with a reciprocal reaction and inducing differentiated cell growth. For this purpose, the active ingredient complex (implant), which can also be produced on an industrial scale, is to be produced outside the body of the living organism and then brought into contact with cells which are to form the biological part. This can occur at a suitable site to which the complex is introduced, either inside the body of the living organism or, outside the body, for instance in a cell culture. In doing this, the complex according to the present invention is brought together with an accumulation of vital, function-capable and specific cells at the desired site.

As is known, biological parts generally consist of specific cells and an extracellular matrix produced by the cell. Since the complex according to the present invention arranges everything for the production of the signals required for the biological part, it is now possible to hold the cells required for this purpose at the site of the complex to the desired geometry, to increase their number and to mature them with a view to the desired functions. Because the active ingredient complex for the promotion of cell growth contains the suitable relevant components for any required partial formation step, its production is guaranteed in its entirety.

Furthermore, with use of the complex according to the invention, same-body cells can be used, so that the known difficulties which arise with the otherwise traditional transplantations are overcome. For example, transmission of illness is no longer possible, no long-term immunosuppression with its grave side effects is required, and the individual living organism remains a genetically uniform entity.

Biological parts take up a certain amount of space for their functional performance. Frequently, their function is connected with a certain geometry within which they fulfill their function. This is also true for the biological parts produced by means of the active ingredient complex of the present invention. The active ingredient complex fulfills this function with the aid of a structural component which on the one hand exerts the space-retaining function and on the other hand allows the assumption of the existence of a geometric form within which the biological part which is produced fulfills its function.

In one preferred embodiment, the active ingredient complex of the present invention is primarily a macromolecular three-dimensional matrix, which together with water and salt can be present in the form of a gel of distinct expansion properties. Thus, for instance, proteoglycan gels may form the matrix. A network of fibers, such as, for instance, different types of collagens or elastin, can also form the structural component. Likewise, combinations of gels with intercalated fibers are suitable composite materials. The structural component for the production of biological parts is manufactured differently for the different intended uses, that it can be used as a fleece, a gel or a liquid gel, which can be cut, milled, or be plastically deformed or cast.

The structural component is adapted to the requirements of the biological part to be repaired or replaced since a certain specificity exists between cellular and the extracellular portions of biological parts. Sources for the production of the structural component are therefore primarily extracellular materials of different tissues or organs. For instance, for the growth of skin cells, cutaneous proteoglycan and fiber proteins are used for the production of the structural component; for the growth of spleen cells, spleen-specific proteoglycans and fibrous proteins are used; for the production of bone, bone-specific proteoglycan and fibrous proteins are used, etc. The structural component can also include metallic, ceramic, vitreous, polymeric or fatty carrier materials, to aid in the modification of the geometric, mechanical, chemical or special properties of the structural component. Thus, the carrier material together with the structural component can be present in solid, porous, membranous, micellar, viscous or liquid form according to the requirements of the particular cells which are to be grown.

In another preferred embodiment of the active ingredient complex according to the present invention, the material displays its capacity for production of the biological parts, its essentially only temporarily. In other words, the active ingredient complex is configured so that it is cyclically controllably decomposable and following production of the biological part is no longer present. The rate of decomposition of the active ingredient complex can thus be controlled by different transverse cross-linking of the polymeric matrix and/or by the addition of (enzyme) inhibitors, immunosuppressants and/or inflammation-inhibiting materials. The inhibitors employed can be low-molecular compounds which occupy the active center of the decomposing enzyme or chelating agents, which bind an essential cofactor of the enzyme to themselves or to the neutralizing antibodies. Other types of inhibiting mechanisms are possible.

As inflammation-inhibiting and/or immunosuppressant additives, the following can be used: inhibitors of phospholipase, such as for instance steroids; inhibitors of cyclooxygenase, such as for instance indomethacin; inhibitors of lipoxygenase, such as for instance nordihydroguaiaretic acid, immunosuppressants of the type including cyclosporin and/or of the type including antithymocyteneglobulin, etc.

According to this invention, living cells of the desired type are to be collected in the region of the structural component. For this purpose, the active ingredient complex further comprises one or more "recruiting components" which cause migration of the cells to the area where the biological part is desired to grow. Chemotaxins are suitable for use as a recruiting component.

The chemotaxins suitable for this use have been described for a number of cells and can be isolated from human, animal, plant or microbial sources or may be produced by chemical synthesis or biotechnical methods. If the structural component produced in vitro is introduced with the recruiting component into an organism and/or is brought into contact with target cells outside the organism, it then builds a concentration gradient in which the target cells are oriented, whereby the relevant recruiting component correlates with the specific identification or recognition structures on the target cells, as receptors. When the biological part to be produced is composed of a plurality of types of cells, the structural component includes a plurality of recruiting components in the form of chemotaxins corresponding to the number of types of cells.

The specificity of the relevant recruiting component for the different target cells as well as the amount of chemotaxic activity is ascertained by research, wherein the directed migration of the desired cells through defined filter pores is measured under the effect of a certain gradient of the chemotaxin in a chamber. The active ingredient system can be biologically standardized relative to its relevant recruiting component by means of researched techniques of this sort, which is important for the industrial production of the active ingredient complex.

Peptides such as N-Formyl-met-leu-phe, or metabolites of arachidonic acid, such as leucotrienes (with the aid of which certain cells, or phagocytes, can be attracted out of the blood) may serve as chemotaxins. Proteins, such as those which attract mesenchyme cells, work chemotaxically especially on connective tissue cells.

In addition to the specificity of the recruiting component for the desired target cells and the amount of chemotaxic activity, the time duration of the activity during which the chemotaxic concentration gradient is built up is also specific and is of considerable length. This kinetic mechanism is adapted to the requirements for the promotion of cell growth by the active ingredient complex according to the present invention by means of a controllable liberation of the relevant recruiting component from the structural component. In doing this at this point, the rate of decomposition of the structural component plays a role, as does the type of connection between the structural component and the relevant recruiting component, dependent for instance on whether there is a covalent or an associative linkage. With covalent linkage, slower synthesis and longer maintenance of the chemotaxic gradients is attained than with merely associative linkage made up of ionic forces or hydrogen bonds. The regrowth of the cells, however, for the most part, occurs more rapidly than the decomposition of the structure component, since the infused cells are quite essential for decomposition of the proteoglycan/collagen material.

Following migration of the cells into the structural component, these cells must then be attached to the structural component, in order to prevent their emigration into the environment and to guarantee a stable architecture of the biological part which is produced. For this purpose, the active ingredient complex includes one or more adhesion components, by means of which the infused cells can be fixed at the site of the structural component. Thus, the adhesion components "anchor" the cells to the structural component. Such adhesions are known as having a certain anchoring specificity. Examples of adhesion components are fibronectin and laminin, which allow connective tissue or epithelial cells to be anchored to the structural component. Numerous other adhesion factors of different specificity may be used depending on the type of cells to be produced with the active ingredient complex according to the present invention. Among others, this group includes the cell adherence molecules L-CAM, N-CAM, cytotactin, tenascin, laminin, fibronectin, collagen types IV, V, VII, as well as synthetic peptides, and the partial sequences of different adhesions represent the matrix, and transmembrane protein compounds, such as for instance integrin.

To increase the specificity of attachment of the desired cells to the structural component during production of the biological parts, antibodies inhibiting undesired adhesion components can be introduced. The biological activity of the adhesion components can be measured in adherence tests of various types (e.g., by means of centrifugal forces, etc.) and thus can be standardized for the entire active ingredient complex.

Frequently, the cells fixed by suitable adhesions and chemotaxically attracted to the area of the structural component for production of the biological part are insufficient in number to constitute the biological part. Also, the mobile cells available in an organism for this process are found for the most part in an insufficiently mature state to fulfill all of the functions of a biological part. They frequently represent precursors or parent cells out of which the functioning mature cells of the biological part to be produced must then develop. For this purpose, the active ingredient complex, according to the invention, has at least one growth and/or maturation component, preferably in the form of one or more cytokines, under the effect of which the number of infused cells is increased and a maturation of the cells occurs.

Cytokines are materials of distinct chemical structure which are characterized in that they cooperate in reciprocal reaction with cells and influence the splitting and growth of cells as well as their maturation and biosynthesis. Cytokines thus have a hormone-like effect, but do not display this quality from a distance as hormones do, but rather only in localized areas, which is advantageous in the production of biological parts, since this is a localized process.

A great number of different cytokines of different specificity are known. These can be used to influence cell growth, differentiation and maturation and also to influence the metabolism of the infused cells which are introduced as other components in the active ingredient system according to the invention. The specificity of the cytokines for certain cells is determined by the presence of corresponding receptors on the target cells, whereby the interaction of a cytokine with the receptor triggers the resulting cellular reaction. The receptors on the target cells described in this case are found in membrane proteins, which pass into reciprocal reaction with the chemotaxin which is being used, link with it and invade the cell. With recycling of the receptors they are again available for linkage with chemotaxins.

Analogously, with the receptors for the cytokines being introduced, it has to do only with a different specificity, while with the same reciprocal reaction mechanism. While the linkage of the chemotaxin leads to directed movement of the target cells, the linkage of the cytokines to the corresponding receptor of the target cell results in growth and/or differentiation. Frequently, the receptors are not yet characterized molecularly, so that they are known only by their specificity for the relevant ligands (chemotaxicum, cytokine, etc.).

Therefore, not infrequently, stimulating or inhibiting of sequential processes can be triggered at the cells, according to the specificity of the relevant cytokine and target cells. The desired cellular reaction of the cytokine in terms of reciprocal reaction for the production of biological parts is generally connected with a dual signal transmission, so that in an advantageous manner at least two cytokines are used in the active ingredient complex according to the present invention, in order to attain both growth and differentiation. Following interaction with a cytokine, many cells produce more cytokines and release them, whereby the cells themselves can thus be stimulated or inhibited the (so-called autocrine mechanism). Frequently, the specificity of the cells for certain cytokines is modified with individual differentiation steps, so that no further interaction can occur, or the reciprocal reactions of a sequential reaction can change over from a stimulating to an inhibiting cellular reaction. The properties of a number of cytokines are known, so that the cytokine effect can likewise be standardized in the active ingredient system.

Some examples of cytokines included in the production of blood, the factor stimulating colonies; in the production of connective tissue, the fibroblasts growth factor; in the production of skin, the epidermal growth factor; in the production of cartilage, the cartilage-inducing factor; in the production of spleen or lymph nodes, the lymphocytes-activating factor as well as spleen peptide; for the production of thymus, the T-cells growth factor as well as thymus peptide; for the production of bone, the bone growth factor as well as the transforming growth factor; for the production of blood vessels, the angiogenesis factor. Furthermore, the following cytokines are also used: interleukins, growth factors similar to insulin, tumor necrosis factor, prostaglandins, leukotrienes, transforming growth factors, growth factor deriving from thrombocytes, interferons, and growth factors deriving from endothelial cells.

Since biological parts are composed most often of a plurality of cell types, combinations can occur. Thus, for instance, the formation of blood vessels is important for blood supply to the biological part being produced, so that accelerated vessel-formation is promoted by addition of an angiogenesis factor as cytokine component of the active ingredient system. Similarly, accelerated formation of nerve connections can be important, and can be realized by a corresponding introduction of additional cytokines into the active ingredient complex.

EXAMPLES

Hereinafter the invention is to be explained in greater detail relative to two exemplary embodiments.

Example 1
Preparation of Active Ingredient Complex for Organogenesis of Skin

Human or animal skin is disengaged mechanically from the epidermis. The cutin which is obtained is degreased in six times the amount (w:v) of chloroform/methanol 1:1, deep-frozen in liquid nitrogen and ground in a deep-freeze grinder to a particle size of 400–1000 millimicrons. The skin particles are then dried in a high vacuum (0.05 Torr) at a low temperature, suspended in a 4 M aqueous solution of guanidine chloride and stirred for 12 hours at room temperature. The undissolved portions are discarded and the dissolved portion is very thoroughly dialyzed with respect to water. The precipitated macromolecular network of proteoglycans and skin collagen is washed and dried in a high vacuum at a low temperature. The fleece which is obtained represents the structural components of the active ingredient system according to the present invention for triggering the so-called organogenesis of skin, into which are then introduced the adhesion component, the chemotaxic component (recruiting component), and the growth and maturation component (cytokine). As the adhesion component, fibronectin is worked into the structural component by precipitation, for instance by means of ethyl alcohol, out of aqueous solution and in the presence of the structural component, or else by common lyophilization. The other components are simultaneously doped into the structure component by the same method. For cutaneous organogenesis, a fibroblast growth factor (FGF) is used as well as an epidermal growth factor, in order to simplify the growth of the epidermis and the surface is provided with an additional adhesion factor, in order to simplify attachment of epithelial cells. In this embodiment, laminin is used which specifically allows for attachment of epithelial cells. The active ingredient system produced in this manner is introduced together with an immunosuppressive to promote the organogenesis of skin.

Example 2
Preparation of Active Ingredient for Osteogenesis

Human or animal bone is disengaged from soft parts, the condyles are removed and the diaphyseal portions sawn off lengthwise and separated from the bone marrow. The bone pieces which are obtained are degreased in six time the amount (w:v) of chloroform/methanol (1:1), deep-frozen in liquid nitrogen and ground in a deep-freeze grinder down to a particle size of 400–1000 micromillimeters.

The particles are demineralized in 0.5 N hydrochloric acid, then washed with water until neutralized and dried in a high vacuum at a low temperature.

The bone particles are then suspended in a 4 M aqueous guanidine chloride solution and stirred for 12 hours at room temperature. The undissolved portions are discarded and the dissolved portions are thoroughly dialyzed with respect to water. The precipitated macromolecular network of proteoglycans and bone collagen is washed in water and dried in a high vacuum. The fleece which is obtained represents the structural component according to the present invention of the active ingredient system for triggering osteogenesis.

An adhesion obtained from the guanidine chloride solvent fraction serves as the component, allowing for attachment of osteoblasts and their precursor cells to the structural component. The recruiting component is a protein which likewise is isolated from bone, and the active component is identified by Boyden chamber experiments. The adhesion component and the recruiting component form a chelate acting with the structural component, which carries out the attachment and settling of bone-forming cells. The chelating agent is produced by precipitation or lyophilization of the components.

For dual transmission of the growth and maturation signals, basic fibroblast growth factor and transforming growth factor-beta are doped into the active ingredient complex. For reinforcement of the effect, an antibody can be added to the bone-forming active ingredient complex, acting against catabolic cytokines, such as cachexia. A suitable concentration of the cytokine is inherent in the active ingredient system, in the size range of approximately 10 ppm.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extend required by the appended claims and the applicable rules of law.

I claim:

1. A complex for the growth of bony tissue or bone comprising:
   a bone derived structural component comprising a macromolecular three-dimensional matrix derived from bone-specific proteins;
   at least one bone derived chemotactic component for recruiting bone growth cells to said matrix;
   at least one bone derived adhesion component for adhering said cells to said matrix, wherein said adhesion component binds to said protein matrix and to specific receptors of said bone growth cells; and
   at least one bone derived bone growth factor.

2. The complex of claim 1, wherein said adhesion component is selected from the group consisting of fibronectin, tenascin, cytotactin, laminin, chondroinectin, collagen types IV, V, VII, N-CAM, L-CAM, and integrin.

3. The complex of claim 1, wherein said growth factor is taken from the group consisting of fibroblast growth factor and transforming growth factor-beta.

4. The complex of claim 1, wherein said chemotactic component is identifiable by a chamber with a porous filter.

5. The complex of claim 1, wherein said chemotactic component comprises a peptide.

6. The complex of claim 1, wherein said chemotactic component is water soluble.

7. The complex of claim 1, wherein said adhesion component is water insoluble.

8. The complex of claim 1, wherein said growth factor is bound to said structural component.

* * * * *